(12) United States Patent
San et al.

(10) Patent No.: US 7,935,511 B2
(45) Date of Patent: *May 3, 2011

(54) AEROBIC SUCCINATE PRODUCTION IN BACTERIA

(75) Inventors: Ka-Yiu San, Houston, TX (US); George N. Bennett, Houston, TX (US); Henry Lin, Thousand Oaks, CA (US)

(73) Assignee: Rice University, Houston, TX (US)

(*) Notice: Subject to any disclaimer, the term of this patent is extended or adjusted under 35 U.S.C. 154(b) by 699 days.

This patent is subject to a terminal disclaimer.

(21) Appl. No.: 11/763,424

(22) Filed: Jun. 14, 2007

(65) Prior Publication Data

US 2007/0249028 A1 Oct. 25, 2007

Related U.S. Application Data

(62) Division of application No. 10/987,511, filed on Nov. 12, 2004, now Pat. No. 7,244,610.

(60) Provisional application No. 60/520,216, filed on Nov. 13, 2003, provisional application No. 60/599,956, filed on Aug. 9, 2004.

(51) Int. Cl.
C12N 1/20 (2006.01)
C12N 1/12 (2006.01)
C12N 15/00 (2006.01)
C12N 15/74 (2006.01)
C12P 7/48 (2006.01)
C12P 4/46 (2006.01)

(52) U.S. Cl. ............... 435/252.33; 435/144; 435/145; 435/252.1; 435/252.3; 435/440; 435/471; 435/488

(58) Field of Classification Search .................. None
See application file for complete search history.

(56) References Cited

U.S. PATENT DOCUMENTS

| | | |
|---|---|---|
| 5,393,615 A | 2/1995 | Corey et al. |
| 5,520,786 A | 5/1996 | Bloczynski et al. |
| 6,455,284 B1 | 9/2002 | Gokarn et al. |
| 6,743,610 B2 | 6/2004 | Donnelly et al. |
| 7,223,567 B2 | 5/2007 | Ka-Yiu et al. |
| 7,244,610 B2 | 7/2007 | San et al. |
| 7,262,046 B2 | 8/2007 | Ka-Yiu et al. |
| 2003/0087381 A1* | 5/2003 | Gokarn et al. ............ 435/69.1 |
| 2005/0042736 A1 | 2/2005 | San et al. |
| 2006/0073577 A1 | 4/2006 | Ka-Yiu et al. |
| 2006/0141594 A1 | 6/2006 | San et al. |

OTHER PUBLICATIONS

Abdel-Hamid, A.M., et al., Pyruvate oxidase contributes to the aerobic growth efficiency of *Escherichia coli*. Microbiol. 2001, 147:1483-1498.

Chou, C., et al.; Effect of Modulated Glucose Uptake on High-Level Recombinant Protein Production in a Dense *E. coli* Culture; Biotechnol. Prog., vol. 10, pp. 644-647, 1994.

(Continued)

*Primary Examiner* — Robert M Kelly
*Assistant Examiner* — Kelaginamane T. Hiriyanna
(74) *Attorney, Agent, or Firm* — Boulware & Valoir

(57) ABSTRACT

Methods of increasing yields of succinate using aerobic culture methods and a multi-mutant *E. coli* strain are provided. Also provided is a mutant strain of *E. coli* that produces high amounts of succinic acid.

10 Claims, 11 Drawing Sheets

OTHER PUBLICATIONS

Dittrich, C. R.; Vadali, R. V.; Bennett, G. N.; San, K.-Y. Redistribution of metabolic fluxes in the central aerobic metabolic pathway of *E. coli* mutant strains with deletion of the ackA-pta and poxB pathways for the production of isoamyl acetate. 2004.

Gokarn, R. R.; Eiteman, M. A.; Altman, E. Expression of pyruvate carboxylase enhances succinate production in *Escherichia coli* without affecting glucose uptake rate. Biotech. Let. 1998, 20, 795-798.

Gokarn, R. R.; Eiteman, M. A.; Altman, E. Metabolic analysis of *Escherichia coli* in the presence and absense of the carboxylating enzymes phosphoenolpyruvate carboxylase and pyruvate carboxylase. Appl Environ Microbiol. 2000, 666, 1844-1850.

Hahm, D. H.; Pan, J. G.; Rhee, J. S. Characterization and evaluation of a pta (phosphotransacetylase) negative mutant of *Escherichia coli* HZB101 as a production host of foreign lipase. Appl Microbiol Biotechnol. 1994, 42, 100-107.

Helling et al., J. Bact. 1971, 105:1224-1226.

Holms, W. H. The central metabolic pathways in *Escherichia coli*: relationship between flux and control at a branchpoint, efficiency of conversion to biomass, and excretion of acetate. Curr Top Cell Regul. 1986, 28, 69-105.

Hong, et al., Biotechnol. Bioeng. 2001, 74:89-95.

Kornberg, H. L. The role and control of the glyoxylate cycle in *Escherichia coli*. Biochem. J. 1966, 99, 1-11.

Kubo et al., J. Biosc. Bioeng. 2000, 6:619-624.

Lin H, Bennett GN, San KY. Effect of carbon sources differing in oxidation state and transport route on succinate production in metabolically engineered *Escherichia coli*. J Ind Microbiol Biotechnol. Mar. 16, 2005; [Epub ahead of print].

Lin H, Bennett GN, San KY. Genetic reconstruction of the aerobic central metabolism in *Escherichia coli* for the absolute aerobic production of succinate. Biotechnol Bioeng. Jan. 20, 2005;89(2):148-56.

Lin H, San KY, Bennett GN. Effect of *Sorghum vulgare* phosphoenolpyruvate carboxylase and *Lactococcus lactis* pyruvate carboxylase coexpression on succinate production in mutant strains of *Escherichia coli*.Appl Microbiol Biotechnol. Nov. 24, 2004; [Epub ahead of print].

Lin H, Vadali RV, Bennett GN, San KY. Increasing the acetyl-CoA pool in the presence of overexpressed phosphoenolpyruvate carboxylase or pyruvate carboxylase enhances succinate production in *Escherichia coli*. Biotechnol Prog. Sep.-Oct. 2004;20(5):1599-604.

Luli, G. W.; Strohl, W. R. Comparison of growth, acetate production, and acetate inhibition of *Escherichia coli* strains in batch and fed-batch fermentations. Applied and Environmental Microbiology. 1990, 56, 1004-1011.

Lin H. et al., Metabolic engineering of aerobic succinate production systems in *Escherichia coli* to improve process productivity and achieve the maximum theoretical succinate yield. Metab Eng. Mar. 2005;7(2):116-27.

Phillips, G. J.; Park, S. K.; Huber, D. High copy number plasmids compatible with commonly used cloning vectors. Biotechniques. 2000, 28, 400-408.

Sunnarborg et al., J. Bacteriol. 1990, 172:2642-2649.

Vemuri, et al., J. Ind. Microbiol. Biotechnol. 2002, 28:325-332.

Vemuri, G. N.; Eiteman, M. A.; Altman, E. Effect of growth mode and pyruvate carboxylase on succinic acid production by metabolically engineered strains of *Escherichia coli*. Appl Environ Microbiol. 2002, 68, 1715-1727.

Yang, Y.T., et al., The effects of feed and intracellular pyruvate levels on the redistribution of metabolic fluxes in *Escherichia coli*. Metabolic Engineering. 2001, 3:115-123.

Yang YT, Peredelchuk M, Bennett GN, San KY. Effect of variation of *Klebsiella pneumoniae* acetolactate synthase expression on metabolic flux redistribution in *Escherichia coli*. Biotechnol Bioeng. Jul. 20, 2000;69(2):150-9.

Yang YT, Aristidou AA, San KY, Bennett GN. Metabolic flux analysis of *Escherichia coli* deficient in the acetate production pathway and expressing the *Bacillus subtilis* acetolactate synthase. Metab Eng. Jan. 1999;1(1):26-34.

Brown, T.D.K., et al., The enzymic interconversion of acetate and acetyl-coenzyme A in *Escherichia coli*. Journal of General Microbiology 102:327-336 (1977).

* cited by examiner

AEROBIC SUCCINATE PRODUCTION IN BACTERIA

PRIOR RELATED APPLICATIONS

This application is a divisional application of U.S. Ser. No. 10/987,511, filed Nov. 12, 2004, which claims the benefit of U.S. Provisional Application No. 60/520,216 filed Nov. 14, 2003 and U.S. Provisional Application No. 60/599,956 filed Aug. 9, 2004.

FEDERALLY SPONSORED RESEARCH STATEMENT

The present invention was developed with funds from the National Science Foundation. Therefore, the United States Government may have certain rights in the invention.

REFERENCE TO MICROFICHE APPENDIX

Not applicable.

FIELD OF THE INVENTION

The invention relates to methods of producing large quantities of succinic acid in aerobically-grown microorganisms.

BACKGROUND OF THE INVENTION

Carboxylic acids hold promise as potential precursors for numerous chemicals. For example, succinic acid can serve as a feedstock for such plastic precursors as 1,4-butanediol (BDO), tetrahydrofuran, and gamma-butyrolactone. New products derived from succinic acid are under constant development, with the most notable of these being polyester which is made by linking succinic acid and BDO. Generally, esters of succinic acids have the potential of being "green" solvents that can supplant more harmful solvents and serve as precursors for millions of pounds of chemicals annually at a total market value of over $1 billion. Along with succinic acid, other 4-carbon dicarboxylic acids, such as malic acid, and fumaric acid also have feedstock potential.

Succinic acid can be used as a monomer for the production of various polyesters. It is commercially prepared by hydrogenation of maleic or fumaric acid, and is also produced by aqueous alkali or acid hydrolysis of succinonitrile. Currently more than 15,000 tons of succinic acid are manufactured annually in the United States.

The production of these carboxylic acids from renewable feedstocks (in this case through fermentation processes) is an avenue to supplant the more energy intensive methods of deriving such acids from nonrenewable sources. It has long been known that a mixture of acids are produced from *E. coli* fermentation. However, for each mole of glucose fermented, only 1.2 moles of formic acid, 0.1-0.2 moles of lactic acid, and 0.3-0.4 moles of succinic acid are produced. As such, efforts to produce carboxylic acids fermentatively have resulted in relatively large amounts of growth substrates, such as glucose, not being converted to desired product. Anaerobic production of succinate is hampered primarily by the limitations of NADH availability, slow cell growth and production.

Metabolic engineering has the potential to considerably improve process productivity by manipulating the throughput of metabolic pathways. Specifically, manipulating enzyme levels through the amplification, addition, or deletion of a particular pathway can result in high yields of a desired product.

SUMMARY OF THE INVENTION

An embodiment of the invention is directed to a method of producing succinic acid in an aerobic culture by supplying a mutant strain of *E. coli* bacteria that produces succinic acid from the glucose substrate in a ratio of at least 0.6:1, preferably 0.8:1, and most preferred 1:1 contacting the bacteria with a glucose substrate, allowing the bacteria to metabolize the glucose under aerobic conditions and isolating and recovering the succinic acid from the bacteria.

A further embodiment of the invention is directed to a method of producing succinic acid in an aerobic culture by supplying a pentamutant strain of *E. coli* bacteria with a glucose substrate, said bacteria containing mutations for the five genes sdhAB, poxB, ackA-pta, icd and iclR, wherein the mutations cause the organism to contain a mutant succinate dehydrogenase, a mutant pyruvate oxidase, a mutant acetate kinase-phosphotransacetylase, a mutant isocitrate dehydrogenase and a mutant aceBAK operon repressor system. This strain produces succinic acid from the glucose substrate in a ratio of between 0.6:1-1:1 succinic acid to substrate. The bacteria are fed glucose which is metabolized under aerobic conditions and the succinic acid is isolated and recovered from the bacteria.

Another embodiment of the invention is directed to a method of producing succinic acid in an aerobic culture by supplying a mutant strain of *E. coli* bacteria with a glucose substrate, wherein the bacteria contain mutations for the six genes sdhAB, poxB, ackA-pta, icd, iclR and ptsG. The mutations cause the organism to contain a mutant succinate dehydrogenase, a mutant pyruvate oxidase, a mutant acetate kinase-phosphotransacetylase, a mutant isocitrate dehydrogenase, a mutant aceBAK operon repressor system and a mutant glucose phosphotransferase system.

Another embodiment of the invention is directed to a method of producing succinic acid in an aerobic culture by supplying a mutant strain of *E. coli* bacteria with a glucose substrate, wherein the bacteria contain mutations for the four genes sdhAB, poxB, ackA-pta, and iclR. The mutations cause the organism to contain a mutant succinate dehydrogenase, a mutant pyruvate oxidase, a mutant acetate kinase-phosphotransacetylase and a mutant aceBAK operon repressor system.

In certain embodiments of the invention, the above tetramutant strain contains an additional mutation to the gene ptsG, which encodes the glucose phosphotransferase system.

In other embodiments of the invention, the tetramutant strain is transformed with a plasmid that overexpresses a gene encoding a mutant form of phosphoenolpyruvate carboxylase.

BRIEF DESCRIPTION OF THE DRAWINGS

The accompanying drawings which are incorporated in and constitute a part of this specification exemplify the invention and together with the description, serve to explain the principles of the invention.

DESCRIPTION OF EMBODIMENTS OF THE INVENTION

Reference will now be made in detail to embodiments of the invention, examples of which are illustrated in the accompanying drawings.

The terms "succinate" and "succinic acid" are used interchangeably herein.

As used herein, the term "mutant strain" refers to a non-wild type strain. In certain embodiments of the invention, a strain containing a mutant version of a gene may exhibit greater expression of that gene relative to the wild type counterpart, i.e, an increased activity mutant. In other embodiments of the invention, a mutant strain may be a reduced activity strain.

An embodiment of the invention provides for the increased production of succinic acid in bacteria via aerobic metabolic pathways.

A further embodiment of the invention provides increased carbon flow from the pyruvate node to the glyoxylate cycle by overexpression of pyruvate carboxylase and/or malic enzyme.

In certain embodiments of the invention the increased expression of glyoxylate cycle enzymes including but not limited to, citrate synthase, aconitase, isocitrate lyase and malate synthase, facilitates the increased production of succinic acid.

An embodiment of the invention utilizes the increased production of phosphoenolpyruvate carboxylase to cause an increase in the production of succinate.

Figure 1:
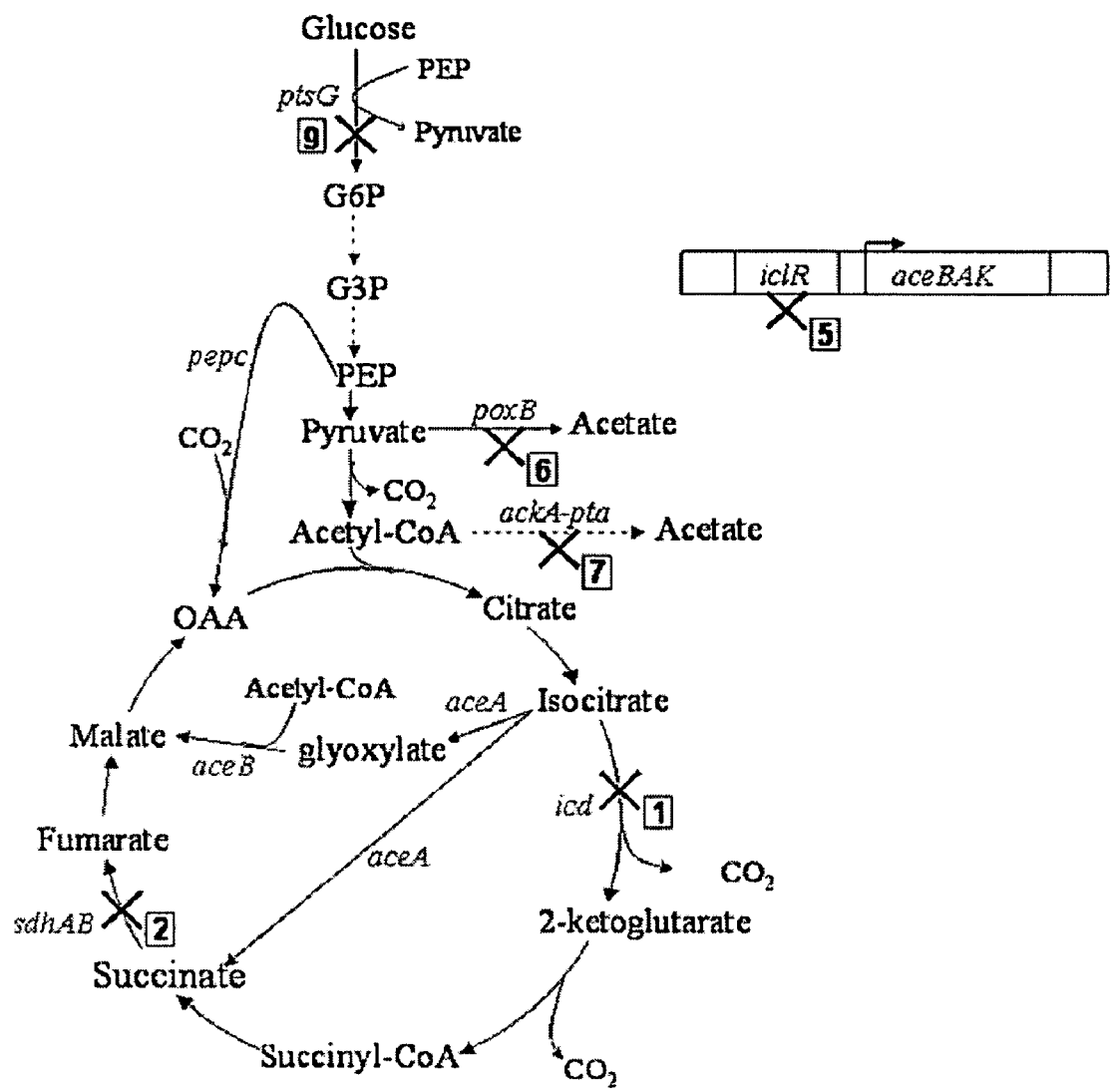
FIG. 1 depicts the genetic engineering of glycolysis, TCA cycle, and glyoxylate bypass in the development of aerobic succinate production systems. 1 is icd knockout, 2 is sdhAB knockout, 5 is iclR knockout, 6 is poxB knockout, 7 is ackA-pta knockout, and 9 is ptsG knockout.

FIG. 1 shows the involvement of several enzymes in the increased production of succinate. In certain embodiments of the invention, certain of the genes encoding one or more of the enzymes set forth in FIG. 1 are mutated such that a particular gene is inactivated and rendered incapable of producing its respective enzyme protein. First, to make succinate accumulation possible under aerobic conditions, the gene encoding succinate dehydrogenase (sdhAB) is inactivated in a representative *E. coli* strain. The sdhAB gene facilitates the conversion of succinate to fumarate in the tricarboxylic acid (TCA) cycle. Therefore, inactivation of the sdhAB gene, which leads to a total loss of succinate dehydrogenase activity causes an accumulation of succinic acid. Next, two enzymes involved in the synthesis of acetate are inactivated in the sdhAB mutant described above, namely the gene encoding pyruvate oxidase (poxB) that converts pyruvate to acetate, and the genes encoding acetate kinase and phosphotransacetylase (ackA-pta) of the pathway that convert acetyl CoA to acetate. The inactivation of the poxB and ackA-pta genes results in the decreased production of acetate and the increased flux of carbon through the TCA cycle.

To conserve the carbon lost to carbon dioxide ($CO_2$) during the TCA cycle, the glyoxalate bypass is engineered as a detour for succinate production. In an embodiment of the invention, the gene encoding isocitrate dehydrogenase (icd) is inactivated. Because icd catalyzes the formation of α-ketoglutarate, which is an essential metabolite in the aerobic synthesis of succinate via the TCA cycle, the inactivation of icd results in the decreased production of succinate by the oxidative arm of the TCA cycle. Inactivation of icd is one alternative strategy in the design and improvement of aerobic succinate production.

In another embodiment of the invention, the glyoxalate bypass is activated by inactivating the gene (iclR) encoding the aceBAK operon repressor protein, iclR. The aceBAK operon encodes the metabolic and regulatory enzymes of the glyoxalate bypass, i.e., the genes encoding isocitrate lyase (aceA), malate synthase (aceB) and isocitrate dehydrogenase kinase-phosphatase (aceK). Thus, the inactivation of iclR along with the four other mutations results in a pentamutant E. coli strain in which the production of succinate occurs primarily through the glyoxalate bypass. An alternative method of activating the glyoxylate bypass is to overexpress the genes by cloning techniques encoding isocitrate lyase (aceA) and malate synthase (aceB), which are required for the glyoxylate bypass. Overexpressing these two enzymes overcomes the regulation of the iclR gene on the glyoxylate bypass. Cloning of these two genes from other organisms will also enhance the glyocylate pathway.

Figure 2:
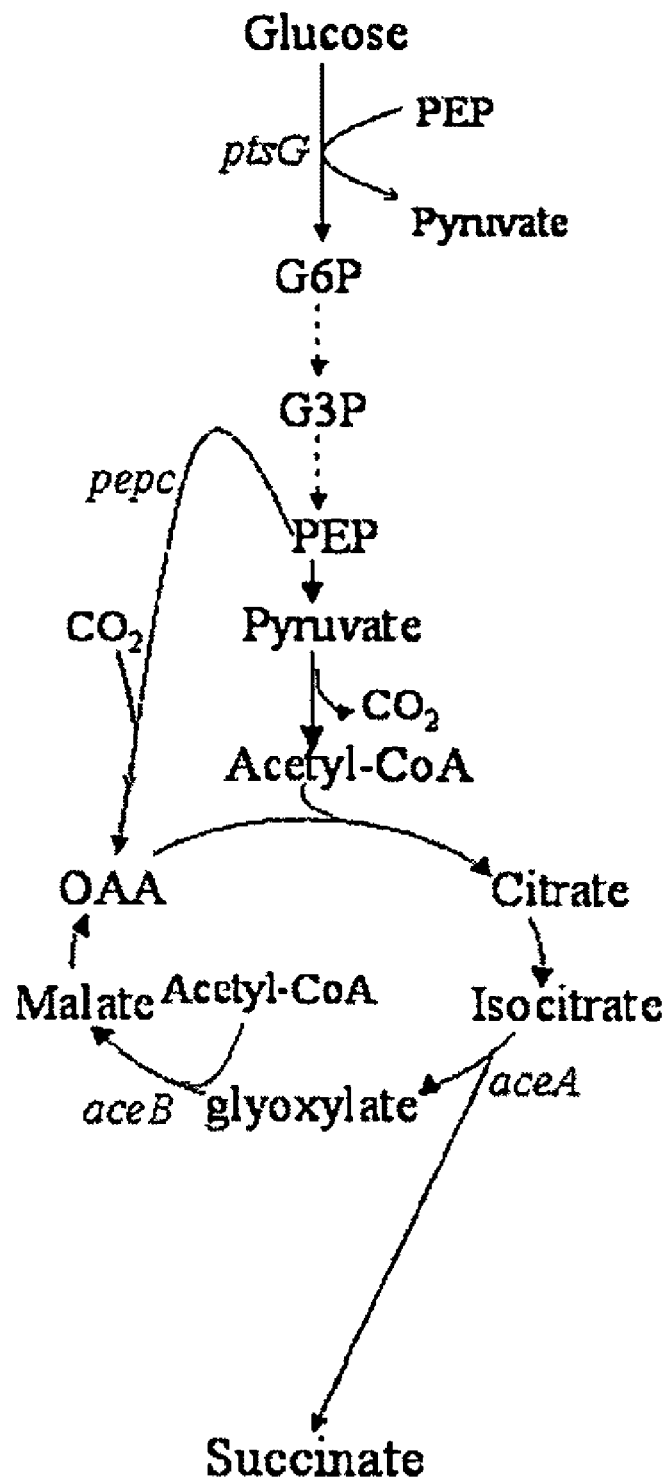
FIG. 2 depicts the aerobic succinate production platform via the glyoxylate cycle in mutant strain HL51276k.

As shown in FIG. 2, the presence of the five genetic mutations discussed above permits the production of succinic acid via the glyoxylate bypass within the aerobic central mechanism. FIG. 2 also shows that the succinate yield can be improved by overexpressing phosphoenolpyruvate carboxylase (PEPC), which converts phosphoenolpyruvate (PEP) to oxaloacetate (OAA) through the fixation of $CO_2$. This increases the OAA pool that is essential for driving the glyoxylate cycle and consequently succinic production.

Figure 3:
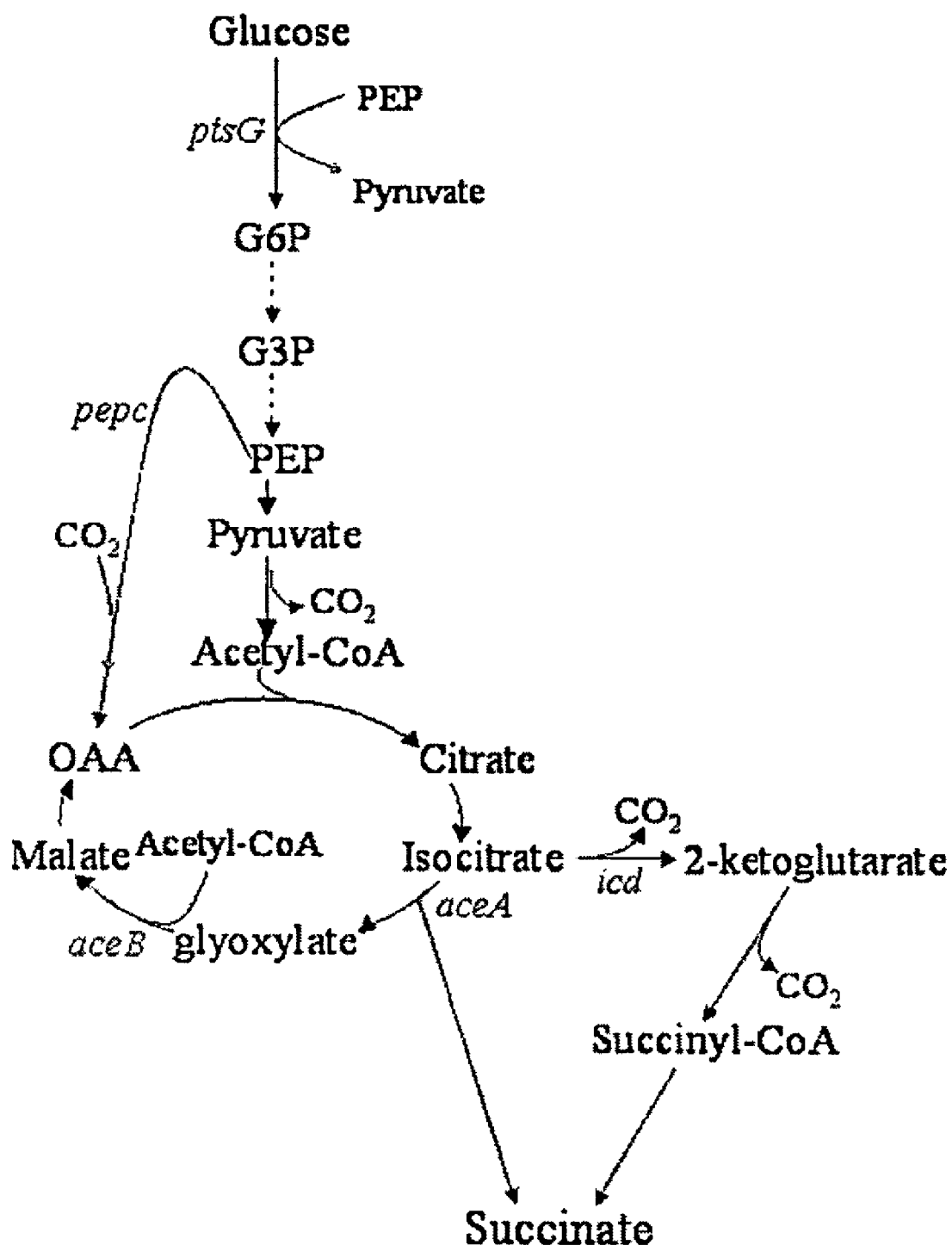
FIG. 3 depicts the aerobic succinate production platform via the two-route system using the glyoxylate cycle and the oxidative branch of the TCA cycle in mutant strain HL2765k.
Figure 4:
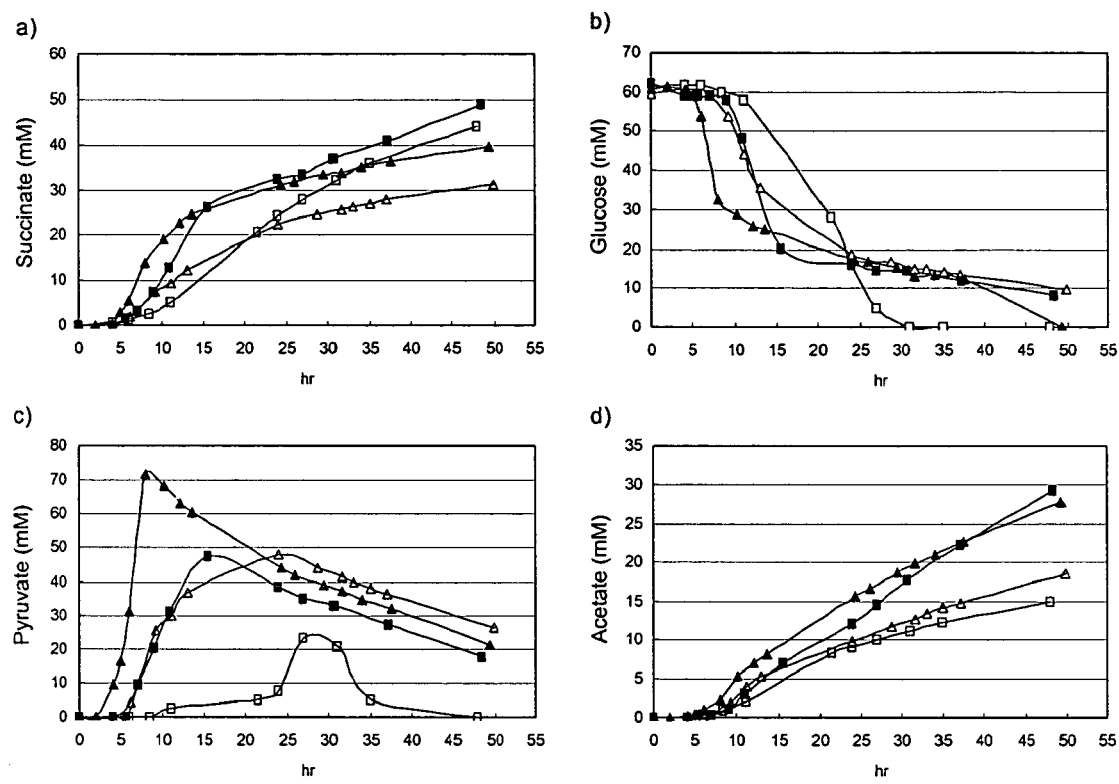
FIG. 4 depicts the metabolite comparison in cultures of mutant strains HL51276k, HL512769k, HL2765k, and HL27659k: a) is succinate production graph; b) is glucose remaining graph; c) is pyruvate production graph; d) is acetate production graph. Solid square (■) is HL27659k; solid triangle (▲) is HL2765k; open square (□) is HL512769k; open triangle (Δ) is HL51276k. Cultivation medium is LB with 2 g/L NaHCO$_3$ and approximately 60 mM of glucose
Figure 5:
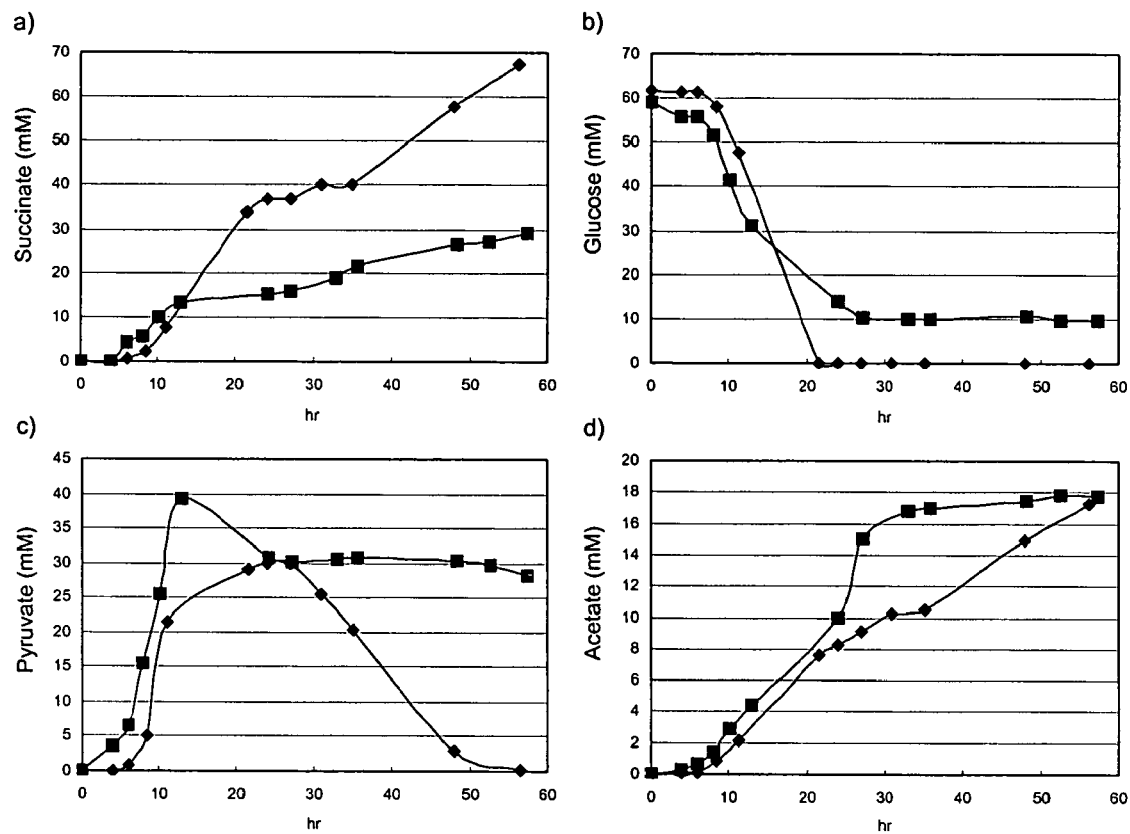
FIG. 5 depicts the metabolite comparison in cultures of mutant strains HL51276k(pKK313) and HL51276k (pKK313C): a) is succinate production graph; b) is glucose remaining graph; c) is pyruvate production graph; d) is acetate production graph. Solid diamond (♦) is HL51276k (pKK313); solid square (■) is HL51276k(pKK313C). Cultivation medium is LB with 2 g/L NaHCO$_3$ and approximately 60 mM of glucose.
Figure 6:
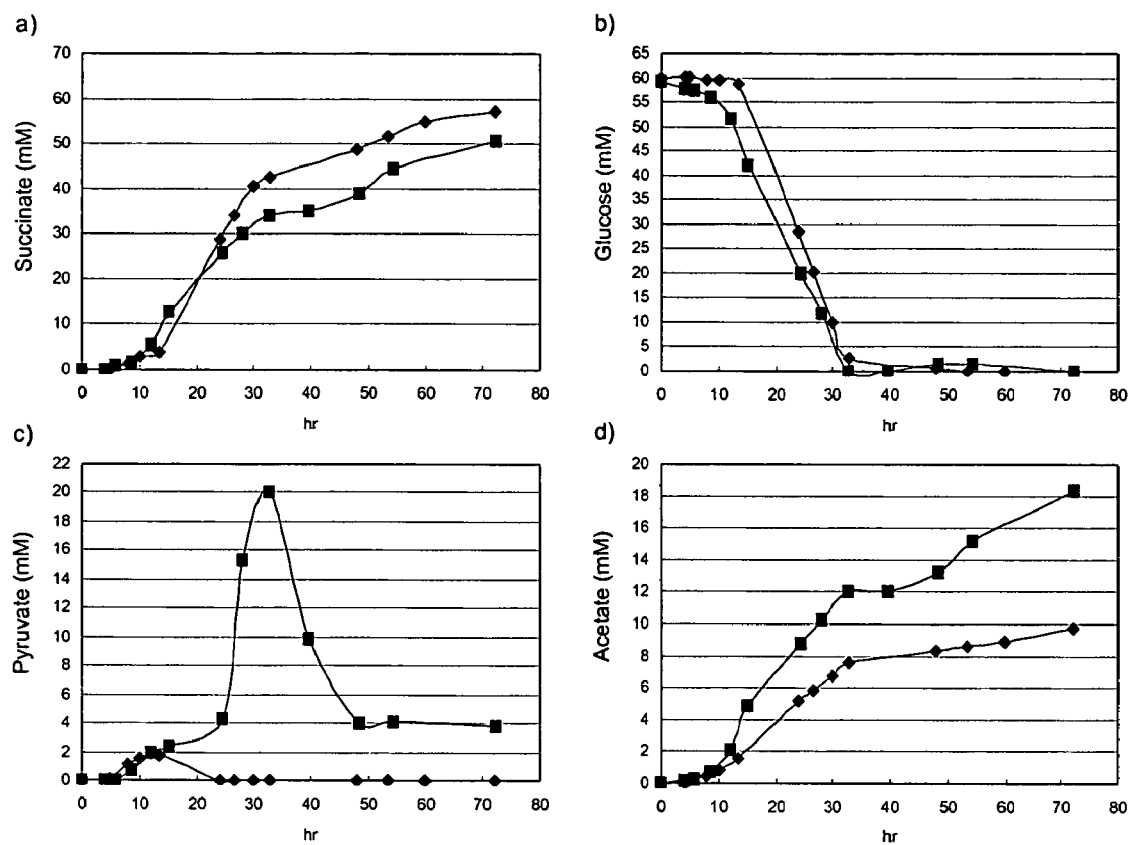
FIG. 6 depicts the metabolite comparison in cultures of strains HL512769k(pKK313) and HL512769k(pKK313C): a) is succinate production graph; b) is glucose remaining graph; c) is pyruvate production graph; d) is acetate production graph. Solid diamond (♦) is HL512769k(pKK313); solid square (■) is HL512769k(pKK313C). Cultivation medium is LB with 2 g/L NaHCO$_3$ and approximately 60 mM of glucose.
Figure 7:
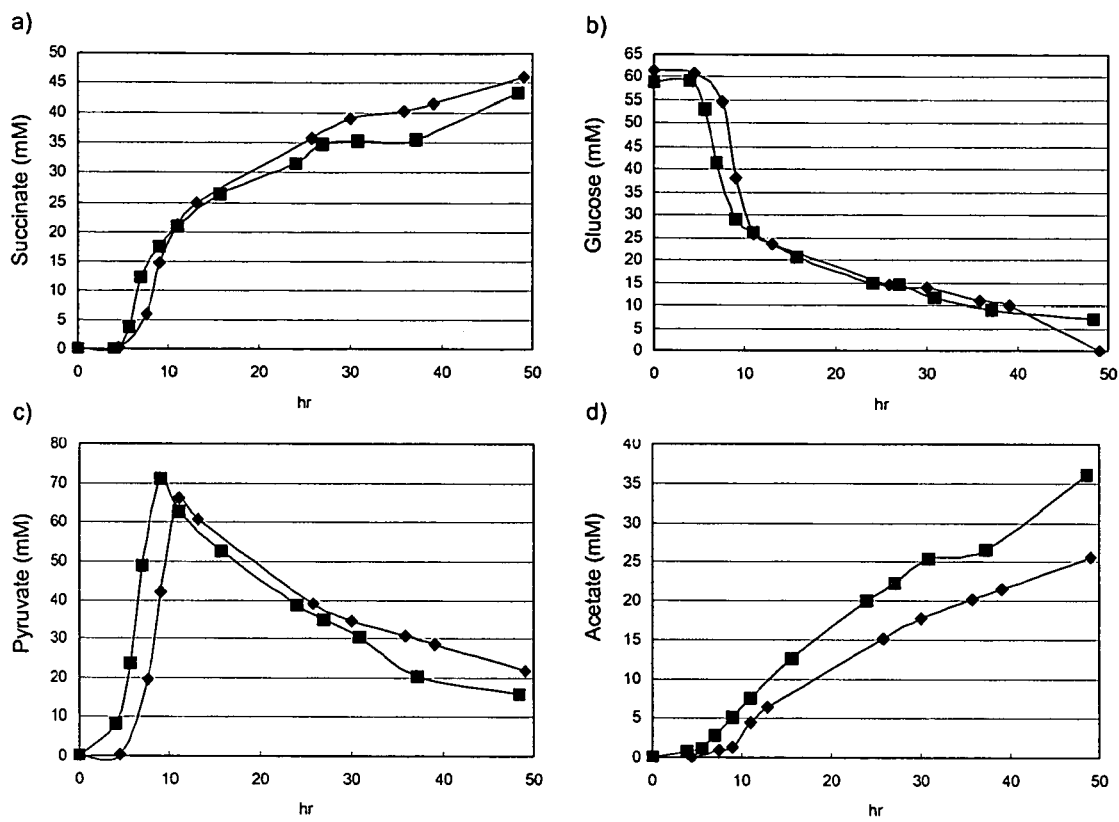
FIG. 7 depicts the metabolite comparison in cultures of strains HL2765k(pKK313) and HL2765k(pKK313C): a) is succinate production graph; b) is glucose remaining graph; c) is pyruvate production graph; d) is acetate production graph. Solid diamond (♦) is HL2765k(pKK313); solid square (u) is HL2765k(pKK313C). Cultivation medium is LB with 2 g/L NaHCO$_3$ and approximately 60 mM of glucose.
Figure 8:
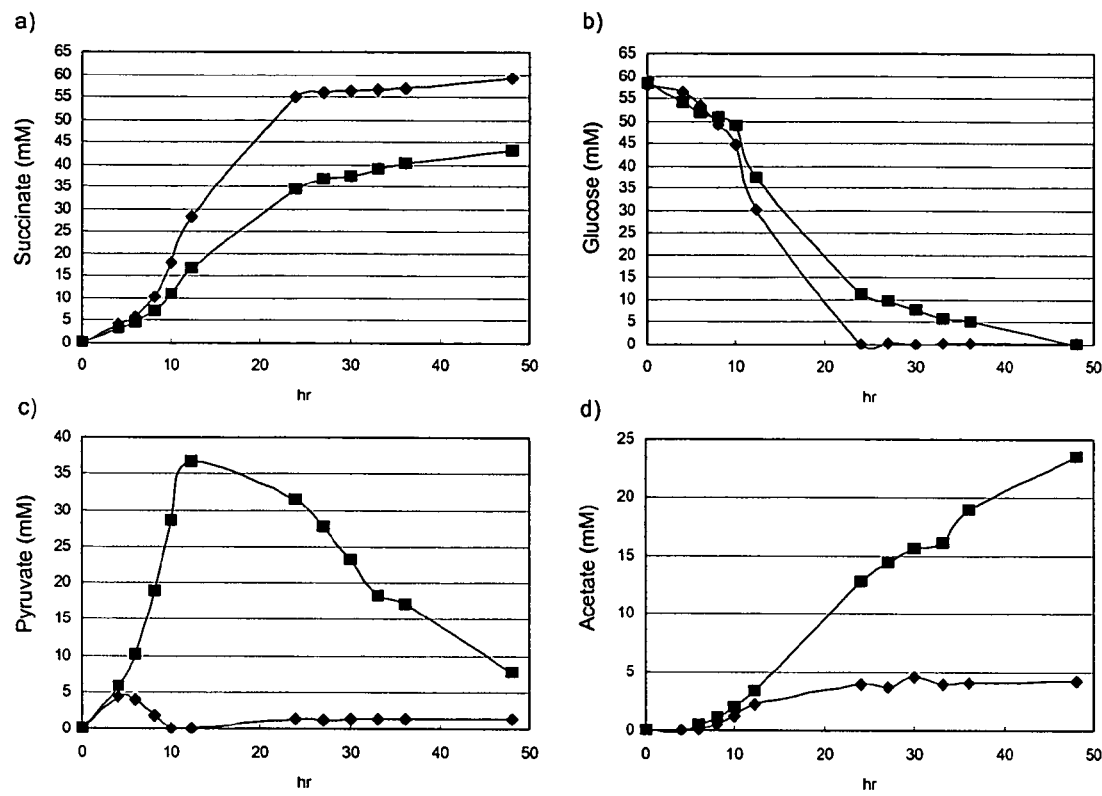
FIG. 8 depicts the metabolite comparison in cultures of strains HL27659k(pKK313) and HL27659k(pKK313C): a) is succinate production graph; b) is glucose remaining graph; c) is pyruvate production graph; d) is acetate production graph. Solid diamond (♦) is HL27659k(pKK313); solid square (■) is HL27659k(pKK313C). Cultivation medium is LB with 2 g/L NaHCO$_3$ and approximately 60 mM of glucose.

FIG. 3 shows another example of a combination of four mutations designed to produce succinate under aerobic conditions. An E. coli strain containing four mutations in the genes sdhAB, poxB, ackA-pta, and iclR is created. The presence of these four mutations creates two routes for succinate production, which branch from the isocitrate node. One route is the glyoxylate cycle and the other route is the oxidative branch of the TCA cycle.

An embodiment of the invention provides a mutant strain of E. coli containing all of the mutations present in the pentamutant strain discussed in FIG. 2, and additionally containing a mutation in the gene (ptsG) encoding the glucose phosphotransferase system.

Another embodiment of the invention provides a mutant strain of E. coli containing all of the mutations present in the pentamutant strain discussed in FIG. 3, and additionally containing a mutation in the gene (ptsG) encoding the glucose phosphotransferase system.

Other embodiments of the invention provide mutant E. coli strains containing mutations in one or more genes encoding enzymes of the tricarboxylic acid cycle and acetate pathways. These enzymes include, but are not limited to, succinate dehydrogenase, isocitrate dehydrogenase, aceBAK operon repressor protein, pyruvate oxidase, acetate kinase and phosphotransacetylase.

In certain embodiments of the invention, pathways from the pyruvate node are overexpressed to channel the increased carbon flow toward the glyoxylate cycle (i.e., pyruvate carboxylase and/or malic enzyme) and thereby improve the rate of succinate production by reducing pyruvate accumulation.

In other embodiments of the invention, manipulation of glucose transport systems may be used to improve carbon throughput to the glyoxylate cycle and thereby increase succinate production. An example of such a manipulation is the inactivation of the glucose phosphotransferase system (ptsG). This manipulation reduces pyruvate accumulation and balances carbon flow towards the glyoxylate cycle by slowing down glucose uptake. The ptsG mutation, therefore, can be added to the combination of gene mutations ($\Delta$sdhAB, $\Delta$poxB, $\Delta$(ackA-pta), $\Delta$iclR, and $\Delta$icd) that thus far created two models of aerobic succinate production strains. FIG. 1 shows the location of the ptsG inactivation relative to the inactivation of the other genes (sdhAB, poxB, ackA-pta, iclR, and icd).

Strains constructed with various gene mutations for aerobic succinate production were transformed with a plasmid containing the gene encoding a mutant phosphoenolpyruvate carboxylase (pepc) from Sorghum. The transformed strains were experimentally shown to achieve the maximum theoretical succinate yield (for wild type bacteria) of one mole per mole glucose. With further optimization, it is predicted that yield will be increased even further, perhaps as high as 2 or 3 to 1, as has been achieved for other systems in our laboratory. Strains also exhibited high succinate productivity under aerobic conditions. See FIGS. 5-8.

The concentration of metabolites such as glucose, pyruvate, acetate and succinate were measured in the mutant strains of the invention. The results are represented in FIGS. 4 and 9-13.

Another example of a manipulation of a glucose transport system is the modification of the galactose permease enzyme, which is encoded by the gal P gene and is responsible for the transport of galactose across the cellular membrane. This modification improves glucose uptake while reducing acetate production.

In an embodiment of the invention, overexpression of the acetyl CoA synthetase enzyme in the presence of externally added acetate is also a potential strategy to further increase the succinate yield. In this modification, the acetyl CoA synthetase increases the acetyl CoA pool by using external acetate.

Example 1

Plasmid Construction

Relevant plasmid constructs were transformed into various E. Coli mutant strains to carry out certain exemplary embodiments of the invention.

The plasmids used in certain embodiments of the invention are set forth in Table 1 below. The mutant bacterial strains (untransformed and transformed) used in certain embodiments of the invention are set forth in Table 2 below.

TABLE 1

| Plasmid | Properties |
|---------|------------|
| pKK313  | S8D mutant Sorghum pepc, $Ap^R$ |
| pKK313C | Control vector of pKK313 with inactive Sorghum pepc, $Ap^R$ |

TABLE 2

| Recombinant Strain | ATCC Deposit No. | Properties |
|---|---|---|
| GJT001 | | Spontaneous cadR mutant of MC4100(ATC35695) Δlac(arg-lac)U169rpsL150relA1ptsF $Sm^R$ |
| HL2k | | GJT001 Δ(sdhAB), $Km^R$ |
| HL26k | | GJT001 Δ(sdhAB-poxB), $Km^R$ |
| HL267k | | GJT001 Δ(sdhAB-poxB-ackA-pta), $Km^R$ |
| HL2671k | | GJT001 Δ(sdhAB-poxB-ackA-pta-icd), $Km^R$ |
| HL26715k | | GJT001 Δ(sdhAB-poxB-ackA-pta-icd-iclR), $Km^R$ |
| HL27615k | | GJT001 Δ(sdhAB-ackA-pta-poxB-icd-iclR), $Km^R$ |
| HL12675k | | GJT001 Δ(icd-sdhAB-poxB-ackA-pta-iclR), $Km^R$ |
| HL51267k | | GJT001 Δ(iclR-icd-sdhAB-poxB-ackA-pta), $Km^R$ |
| HL51276k | | GJT001 Δ(iclR-icd-sdhAB-ackA-pta-poxB), $Km^R$ |
| HL52167k | | GJT001 Δ(iclR-sdhAB-icd-poxB-ackA-pta), $Km^R$ |
| HL51276k | | GJT001(ΔiclR, Δicd, ΔsdhAB, Δ(ackA-pta), ΔpoxB::$Km^R$) |
| HL512769k | | GJT001(ΔiclR, Δicd, ΔsdhAB, Δ(ackA-pta), ΔpoxB, ΔptsG::$Km^R$) |
| HL2765k | | GJT001(ΔsdhAB, Δ(ackA-pta), ΔpoxB, ΔiclR::$Km^R$) |
| HL27659k | | GJT001(ΔsdhAB, Δ(ackA-pta), ΔpoxB, ΔiclR, ΔptsG::$Km^R$) |
| HL51276k(pKK313) | | HL51276k overexpressing S8D mutant Sorghum pepc |
| HL512769k(pKK313) | | HL512769k overexpressing S8D mutant Sorghum pepc |
| HL2765k(pKK313) | | HL2765k overexpressing S8D mutant Sorghum pepc |
| HL27659k(pKK313) | | HL27659k overexpressing S8D mutant Sorghum pepc |
| HL51276k(pKK313C) | | Control strain for HL51276k(pKK313) |
| HL512769k(pKK313C) | | Control strain for HL512769k(pKK313) |
| HL2765k(pKK313C) | | Control strain for HL2765k(pKK313) |
| HL27659k(pKK313C) | | Control strain for HL27659k(pKK313) |

Example 2

Construction of Mutant Strains

Mutant strains derived from a parent E. coli strain, GJT001, were created by mutation of one or more of the genes encoding succinate dehydrogenase (sdh), pyruvate oxidase (poxB), acetate kinase-phosphotransacetylase (ackA-pta), isocitrate dehydrogenase (icd) and the aceBAK operon repressor (iclR), using the one-step inactivation method of Datsenko and Wanner (2000). This method first requires the construction of the single mutations using the phage λ Red recombinase. P1 phage transduction was then used to combine various mutations into one strain. Each mutation has to be added to the strain one at a time before the introduction of the next mutation because the kanamycin cassette has to be removed at each stage to enable selection of the next mutation.

PCR products of the kanamycin cassette gene flanked by FRT (FLP recognition target) sites and homologous sequences to the gene of interest were made using pKD4 as the template. These PCR products were then transformed into the cells by electroporation (Bio-Rad Gene Pulserm™) for insertional inactivation of the gene of interest. These transformed cells carry the plasmid pKD46 that expresses the λ Red system (γ, β, exo) for recombination of the PCR product into the chromosome. Once the kanamycin cassette is inserted, it can be removed using the helper plasmid, pCP20 that expresses FLP. The removal of the FRT-flanked kanamycin cassette leaves behind an 84 base pair insertion cassette.

At each stage of mutation, experiments were performed to test the intermediate mutant for the effect on metabolite production. Throughout the process of constructing the aerobic succinate production system, a library of different mutants with varying types and numbers of mutations was created. All mutants were also verified with genomic PCR after construction to ensure that the gene of interest had been disrupted.

Example 3

Growth of Mutant Strains

Aerobic batch reactor experiments were conducted for all the mutant strains. The medium used is LB with 2 g/L $NaHCO_3$ and approximately 60 mM of glucose. The medium used for inoculum preparation is also LB, except glucose was not supplemented. $NaHCO_3$ was added to the culture medium because it yielded better cell growth and succinate production due to its pH-buffering capacity and its ability to supply $CO_2$. Kanamycin was added to the medium at a concentration of 50 mg/L for strains not harboring plasmids. In strains harboring pKK313 or pKK313C, ampicillin, carbenicillin, and oxacillin were added to the medium at a concentration of 200 mg/L each. Studies have shown that the use of methicillin and ampicillin is effective as a selective pressure in the cultivation of recombinant E. coli. Oxacillin is an analog of methicillin. The use of ampicillin, carbenicillin, and oxacillin in combination during the experiments enforced plasmid retention throughout the aerobic fermentation. IPTG was added at 1 mM to the medium to induce gene expression for plasmids pKK313 and pKK313C.

The initial medium volume is 600 ml in a 1.0-L New Brunswick Scientific Bioflo™ 110 fermenter. A 1% (v/v) inoculum was used from an overnight culture grown from a single colony for 12 hours. The pH was measured using a glass electrode and controlled at 7.0 using 1.5N $HNO_3$ and 2N $Na_2CO_3$. The temperature was maintained at 37° C., and the agitation speed was constant at 800 rpm. The inlet airflow used was 1.5 L/min. The dissolved oxygen was monitored using a polarographic oxygen electrode and was maintained above 80% saturation throughout the experiment. This was to demonstrate that the succinate production systems were working under absolute aerobic conditions.

Example 4

Analytical Techniques

Optical density was measured at 600 nm with a spectrophotometer (Bausch & Lomb Spectronic™ 1001); the culture was diluted to the linear range with 0.15 M NaCl. For analyzing the extracellular metabolites, 1 ml of culture was centrifuged and the supernatant was then filtered through a 0.45-μm syringe filter for HPLC analysis. The HPLC system (Shimadzu-10A Systems, Shimadzu, Columbia, Md.) used was equipped with a cation-exchange column (HPX-87H, BioRad Labs, Hercules, Calif.), a UV detector (Shimadzu™ SPD-10 A) and a differential refractive index (RI) detector (Waters™ 2410, Waters, Milford, Mass.). A 0.6 mL/min mobile phase using 2.5 mM $H_2SO_4$ solution was applied to the column. The column was operated at 55° C. Standards were prepared for glucose, succinate, acetate, and pyruvate for both the RI detector and UV detector, and calibration curves were created. Glucose, succinate, and acetate were measured by the RI detector and pyruvate was measured by the UV detector at 210 nm.

Example 5

Comparison of Metabolite Profiles

Strains HL51276k and HL2765k were grown in bioreactors at 37° C. where the dissolved oxygen was maintained above 80% saturation throughout the experiment. Their metabolite profiles were compared. Results showed that strain HL2765k had a higher succinate production than HL51276k. At approximately 48 hours, the succinate concentration in the HL2765k culture was 40 mM compared to that of the HL51276k culture, which had 31 mM succinate (FIG. 4a). Succinate molar yields at the highest concentration produced were 0.67 for HL2765k and 0.65 for HL51276k. See Table 3 below. HL2765k also had 65% higher volumetric succinate productivity and 12% higher specific succinate productivity than HL51276k.

TABLE 3

| Strain | $Y_{S/G}$ (mol/mol) | $Q_p$ (g/l-hr) | $q_p$ (mg/g-hr) |
| --- | --- | --- | --- |
| HL51276k | 0.65 | 0.057 | 24.04 |
| HL512769k | 0.87 | 0.086 | 35.47 |
| HL2765k | 0.67 | 0.094 | 26.84 |
| HL27659k | 0.78 | 0.130 | 32.82 |
| HL51276k(pKK313C) | 0.61 | 0.048 | 27.54 |
| HL51276k(pKK313) | 1.09 | 0.140 | 44.26 |

TABLE 3-continued

| Strain | $Y_{S/G}$ (mol/mol) | $Q_p$ (g/l-hr) | $q_p$ (mg/g-hr) |
| --- | --- | --- | --- |
| HL512769k(pKK313C) | 0.85 | 0.083 | 38.99 |
| HL512769k(pKK313) | 0.96 | 0.094 | 45.23 |
| HL2765k(pKK313C) | 0.71 | 0.113 | 28.33 |
| HL2765k(pKK313) | 0.75 | 0.111 | 35.54 |
| HL27659k(pKK313C) | 0.74 | 0.106 | 31.14 |
| HL27659k(pKK313) | 0.95 | 0.270 | 73.66 |

In Table 3, $Y_{S/G}$ is the molar succinate yield at the end of fermentation (mole of succinate produced per mole of glucose consumed); $Q_p$ is the average volumetric succinate productivity at the end of fermentation (mass concentration of succinate (g/l) over time (hr)); $q_p$ is the average specific succinate productivity at the end of fermentation (mass of succinate (mg) per mass of biomass (g) over time (hr)).

Strain HL2765k grew to a higher OD (14.27 OD) than strain HL51276k (9.21 OD). HL2765k also had a faster biomass generation rate (0.60 g/l-hr) than HL51276k (0.24 g/l-hr), because its glucose consumption rate is faster than HL51276k. There was pyruvate accumulation in cultures of both strains, which was produced and then consumed (FIG. 4c). HL2765k had a higher pyruvate accumulation in the beginning of fermentation than HL51276k. This is because HL2765k has faster glucose consumption and cell mass generation than HL51276k. The pyruvate was taken up and consumed faster by HL2765k than HL51276k (FIG. 4c). HL2765k also produced acetate faster than HL51276k due to its more rapid glucose consumption rate (FIG. 4d). Strain HL2765k did not have any accumulation of TCA cycle $C_6$ intermediates, whereas strain HL51276k did (data not shown). Comparison of these two strains showed that HL2765k was more robust than HL51276k. Strain HL2765k with two pathways engineered for succinate production has a faster succinate productivity and glucose consumption rate than HL51276k, which only utilizes the glyoxylate cycle for succinate production.

The glucose phosphotransferase system (PTSG) was studied in the two strains HL2765k and HL51276k to examine the possibility of reducing pyruvate and acetate accumulation. By inactivating the phosphotransferase uptake system, pyruvate can no longer be formed from phosphoenolpyruvate (PEP) through the transport of glucose. This genetic manipulation can potentially reduce pyruvate accumulation. Acetate formation occurs because of excess consumption of glucose that the cell is unable to utilize for biomass synthesis or energy requirements, leading to repression of enzymes in the TCA cycle by glucose. The secretion of acetate leads to an uncoupled metabolism. Inactivating ptsG can slow glucose uptake and possibly allow a more balanced glucose metabolism. Inactivation of ptsG has been shown to increase succinate production in pyruvate formate lyase and lactate dehydrogenase mutant strains. This effect is probably due to more PEP being conserved and available for the succinate synthesis pathway, while also generating a slower glucose uptake rate. ptsG was inactivated in the strain HL2765k to form HL27659k and in the strain HL51276k to form HL512769k (hexamutant strain of E. coli) (Table 2). The number 9 represents the inactivation of ptsG (FIG. 1).

Strains HL27659k and HL512769k were grown aerobically under the same batch reactor conditions described earlier for strains HL2765k and HL51276k. The results showed ptsG inactivation did improve succinate production. At approximately 48 hours, HL27659k produced 49 mM succinate compared to HL2765k, which produced 40 mM, and HL512769k produced 44 mM succinate compared to HL51276k, which produced 31 mM (FIG. 4a). At the highest succinate concentration produced, the molar yield was also higher when ptsG was inactivated (0.78 for HL27659k compared to 0.67 for HL2765k, and 0.87 for HL512769k compared to 0.65 for HL51276k) (Table 3). The succinate volumetric productivity and specific productivity at the highest succinate concentration were also higher from cultures of those strains with ptsG inactivation. HL27659k had 38% higher succinate volumetric productivity and 22% higher specific productivity than HL2765k (Table 3). HL512769k had 51% higher succinate volumetric productivity and 48% higher specific productivity than HL51276k (Table 3). The effects of ptsG inactivation improve succinate production more in HL51276k than in HL2765k; this is because there are more bottlenecks in the TCA pathways of HL51276k than in HL2765k (HL51276k has TCA cycle $C_6$ accumulation and HL2765k does not).

ptsG inactivation caused cell growth to be lower due to slower glucose consumption during the exponential phase. HL27659k grew to an OD of 12.59 at the end of its exponential phase compared to HL2765k, which grew to 14.27 OD. HL512769k grew to an OD of 8.31 at the end of its exponential phase compared to HL51276k, which grew to an OD of 9.21 OD. By the end of the exponential phase, the biomass generation rate of strain HL2765k was 0.60 g/l-hr compared to strain HL27659k, which was 0.27 g/1-hr. For strain HL51276k, the biomass generation rate at the end of the exponential phase was 0.24 g/1-hr compared to strain HL512769k, which has 0.13 g/1-hr.

Inactivation of ptsG did reduce pyruvate accumulation in cultures of strains HL2765k and HL51276k. Pyruvate accumulation in HL27659k only reached a maximum concentration of 48 mM compared to HL2765k, which reached 72 mM (FIG. 4c). Strain HL512769k produced a maximum pyruvate concentration of 23 mM, compared to HL51276k, which produced 48 mM (FIG. 4c). In strain HL512769k, there was no pyruvate accumulation after 48 hours. All the glucose was consumed by cultures of all four strains by the end of the fermentation. Inactivation of ptsG also reduced acetate production. HL27659k had a lower acetate production rate than HL2765k in the first 24 hours. By the end of the fermentation though when all the glucose was consumed in the cultures, HL27659k had slightly higher acetate production than HL2765k (FIG. 4d). Acetate production was lower in HL512769k than in HL51276k throughout the fermentation (FIG. 4d). Strain HL512769k accumulated TCA cycle $C_6$ intermediates and strain HL27659k did not. Results showed that ptsG inactivation did improve succinate yield and productivity in cultures of the two strains, HL2765k and HL51276k. Because of the ptsG inactivation, glucose consumption was slowed, which helped reduce pyruvate and acetate accumulation by providing a more balanced metabolism.

Example 6

Overexpession of pepc ptsG inactivation has been shown to improve succinate yield and productivity. Yet in strains HL27659k and HL512769k, the maximum theoretical succinate yield of one mole produced per mole glucose consumed has not been obtained. This indicates that the aerobic production systems can be further optimized. PEPC converts PEP to OAA through a carboxylation reaction with $CO_2$ (FIG. 1). OAA is an important precursor for the synthesis of succinate. Overexpression of pepc in E. coli has been shown to increase succinate production. Therefore, overexpression of pepc in the aerobic succinate production systems should improve succinate yield and productivity, and at the same time further reduce pyruvate and acetate accumulation. A mutant pepc from Sorghum was overexpressed on plasmid pKK313. (Table 1) in the four strains HL51276k, HL512769k, HL2765k, and HL27659k. This mutant PEPC is feedback inhibition resistant to malate (Wang et al., 1992). This mutation is advantageous for the aerobic succinate production systems because even though succinate is not being formed by the reduction of malate as in anaerobic conditions, malate is still present and required in the glyoxylate cycle as the precursor of OAA (FIGS. 2 and 3). The control plasmid for pKK313 is pKK313C (Table 1), which was also transformed into the four mutant strains. The mutant strains carrying the plasmids were grown aerobically in bioreactors at 37° C. where the dissolved oxygen was maintained above 80% saturation throughout the experiment. Mutant strains harboring pKK313 were compared in terms of their metabolite production and succinate yield and productivity with the same mutant strains harboring pKK313C.

Overexpression of the mutant Sorghum pepc in strains HL51276k, HL512769k, HL2765k, and HL27659k was effective in increasing succinate production. The succinate production of cultures of strain HL51276k(pKK313) was 130% higher than those of strain HL51276k(pKK313C) at the end of the fermentation when all the glucose had been consumed (FIG. 5a). Cultures of HL27659k(pKK313) had 37% higher succinate production than its control strain HL27659k(pKK313C) (FIG. 8a). The increase in succinate production of cultures of strains HL512769k(pKK313) and HL2765k(pKK313) compared to their respective controls was not as substantial as that found for HL51276k(pKK313), although their succinate concentrations were continuously higher than their controls throughout the production phase (FIGS. 6a and 7a). In strains with high levels of PEPC, the molar succinate yields for strains HL51276k(pKK313), HL512769k(pKK313) and HL27659k(pKK313) all reached the maximum theoretical value of one mole of succinate produced per mole of glucose consumed (Table 3). The molar succinate yield for strain HL2765k(pKK313) was 0.75 compared to 0.71 for its control strain HL2765(pKK313C) (Table 3). Overexpression of pepc therefore, was not as effective in increasing the succinate yield in strain HL2765k as in the other strains. The specific succinate productivity was higher in all the strains overexpressing pepc; strain HL51276k (pKK313) was 61% higher than its control; HL512769k (pKK313) was 16% higher, HL2765k(pKK313) was 25% higher, and HL27659k(pKK313) was 137% higher than respective their controls carrying pKK313C (Table 3). These results showed that high expression of mutant Sorghum pepc was very effective in improving succinate yield in the mutant E. coli host strains and successfully optimized three of the aerobic production systems (HL51276k, HL512769k, and HL27659k) to produce the maximum theoretical succinate yield of 1.0 mole per 1.0 mole glucose consumed. Although cultures of strains HL51276k(pKK313), HL512769k (pKK313), and HL27659k(pKK313) all achieved the maximum theoretical succinate yield, they still varied in their efficiency. Among the three strains, HL27659k(pKK313) was the most efficient. Fermentation showed substantially higher volumetric succinate productivity (0.27 g/1-hr) and specific productivity (73.66 mg/g-hr) than the other two strains (Table 3). The volumetric succinate productivity for cultures of HL27659k(pKK313) was 93% and 187% higher than strains HL51276k(pKK313) and HL512769k(pKK313), respectively. As for specific succinate productivity, cultures of HL27659k(pKK313) were 66% and 63% higher than those of strains HL51276k(pKK313) and HL512769k(pKK313), respectively. These results demonstrate that fermentations of strain HL27659k(pKK313), with its 1.0 mol/mol succinate yield, is a more efficient and robust aerobic succinate production system for large-scale production than the other systems.

Overexpression of pepc was also effective in reducing pyruvate production. Maximum pyruvate produced in cultures of strains HL51276k(pKK313) and HL2765k(pKK313) was lower than their controls carrying pKK313C (FIGS. 5c and 7c). In cultures of strains HL512769k(pKK313) and HL27659k(pKK313), pyruvate accumulation was virtually eliminated (FIGS. 6c and 8c). These results demonstrate that overexpression of pepc coupled with ptsG inactivation was the most effective in reducing pyruvate accumulation, thus providing more efficient carbon throughput.

Acetate production was reduced in cultures of the mutant strains with the high levels of PEPC. Cultures of strain HL512769k(pKK313) had a 47% reduction, HL2765k (pKK313) had a 29% reduction, HL27659k(pKK313) had an 82% reduction compared to cultures of their respective control strains carrying pKK313C (FIGS. 6d, 7d and 8d). Acetate production for strain HL51276k(pKK313) was lower than HL51276k(pKK313C) throughout production, but their final acetate concentrations at the end of fermentation after all the glucose was consumed were similar (FIG. 5d). Cultures of strain HL27659k(pKK313) exhibited the lowest acetate level produced among all the four strains (below 5 mM) and also had little pyruvate accumulated (below 2 mM). Its main product was succinate at 60 mM at the end of fermentation when all the glucose was consumed, equivalent to approximately 1.0 mol succinate/mol glucose.

The culture conditions of the mutant strains developed and studied for aerobic succinate production, thus far, have not been optimized for production. The calculation of succinate yield and productivity (Table 3) has included both the growth phase (biomass generation) and the production phase. These aerobic systems are efficient and practical because they do not require separation of the growth phase from the production phase for succinate production as in conventional anaerobic succinate production systems. Nevertheless, the culture conditions of the aerobic succinate production systems can be further optimized to improve process productivity.

Figure 9:
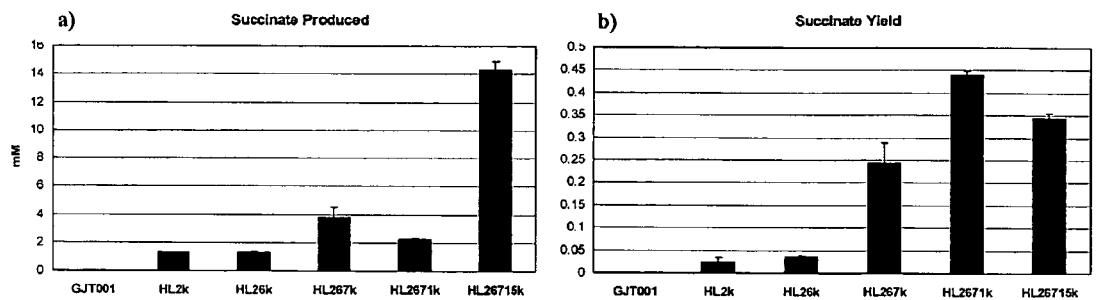
FIG. 9 depicts succinate production in mutant strains: a) Succinate production at each incremental step of incorporating mutations into the parental strain. The strain containing the five mutations combined represents the aerobic succinate production system. Each number designates a specific knock-out in the pathways as shown by FIG. 1.; b) Succinate yield as a result of each incremental addition of mutation to the parental strain. Yield is mole of succinate produced per mole of glucose consumed. Mean and standard deviation were calculated based on duplicate experiments.
Figure 10:
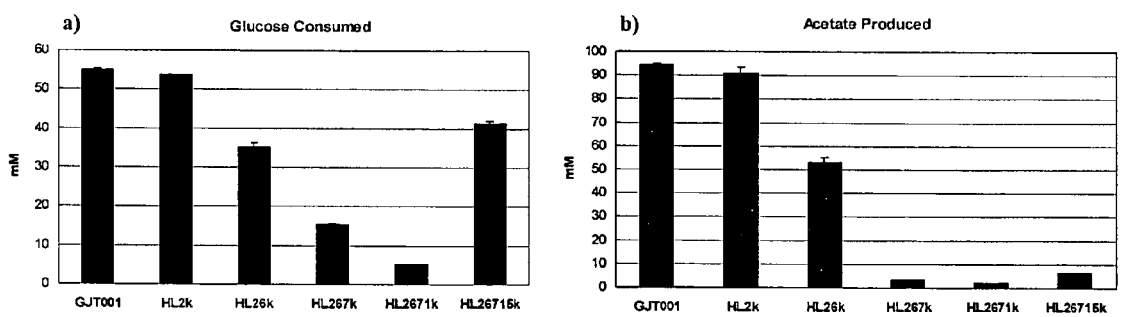
FIG. 10 depicts glucose and acetate metabolism in mutant strains: a) Glucose consumed by the parental strain and the five mutant strains after 24 hours of culture; b) Acetate produced by the parental strain and the five mutant strains after 24 hours of culture. Mean and standard deviation were calculated based on duplicate experiments.
Figure 11:
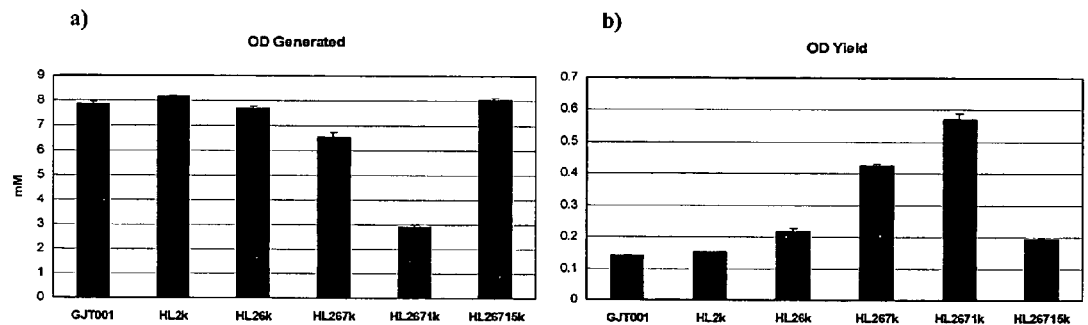
FIG. 11 depicts the growth of modified strains in standard media: a) Growth of the parental strain and the five mutant strains after 24 hours. OD measured at 600 nm.; b) OD yield after 24 hours of culture. Yield is OD generated per mole of glucose consumed. Mean and standard deviation were calculated based on duplicate experiments.
Figure 12:
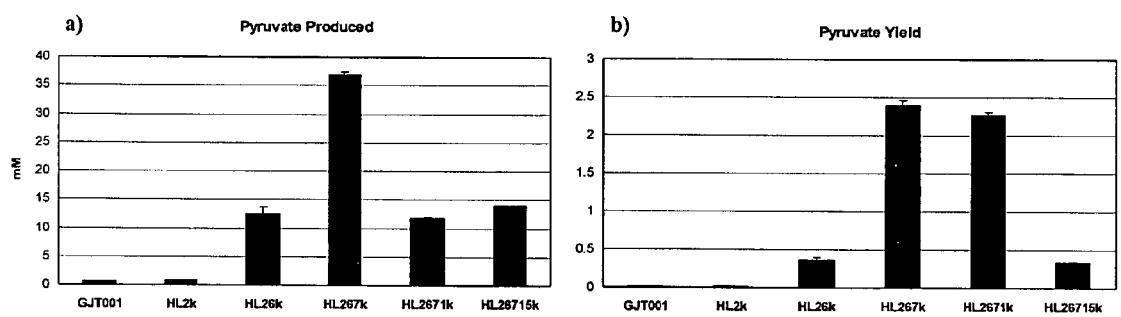
FIG. 12 depicts pyruvate metabolism in modified strains: a) Accumulation of pyruvate by the parental strain and the five mutant strains after 24 hours of culture; b) Pyruvate yield after 24 hours of culture. Yield is mole of pyruvate produced per mole of glucose consumed. Mean and standard deviation were calculated based on duplicate experiments.

FIG. 9 shows the results of succinate production and yield from the culture of each mutant strain and the parental strain. In the mutant strain HL2k with only sdh inactivated, succinate accumulated during culture. Succinate accumulation was not possible in the wildtype (GJT001) as shown by zero succinate production (FIG. 9a). Inactivation of the two acetate pathways, poxB and ackA-pta, further increased succinate production and yield as shown by mutant strain HL267k. Next, as dictated by the design strategy, icd was inactivated creating mutant strain HL2671k. When the icd was inactivated, succinate production decreased as expected since the cell probably could no longer use the oxidative arm of the TCA cycle to produce succinate. The amount of succinate produced by HL2671k could be due to the glyoxylate bypass being partially active. The molar succinate yield of HL2671k increased significantly, though, but this was accompanied by a much lower glucose consumption (FIG. 10a). Finally, when the glyoxylate bypass was activated by inactivating iclR, succinate production increased substantially to 14.28 mM with a molar yield of 0.344. This is over a 5-fold increase in succinate production compared to HL2671k. The result is shown by the pentamutant strain HL26715k. At this point, a highly functioning glyoxylate cycle is created. This provides a detour to relieve the carbon flux from the TCA cycle bottleneck created in mutant strain HL2671k. Activating the glyoxylate bypass reconstituted the cycling and replenishment of OAA. As a result, HL26715k showed much higher glucose consumption than the previous three strains containing mutations due to a faster and more efficient carbon throughput (FIG. 10a). The cell growth of HL26715k was also healthy again, and was similar to that of the wildtype parental strain GJT001 (FIG. 11a).

Glucose consumption decreased throughout the first four mutant strains (FIG. 10a). Once HL26715k was created, glucose consumption was much higher due to an active glyoxylate cycle, but still not as high as the wildtype parental strain. This was also the same trend observed for the OD, where HL26715k generated an OD similar to the parental strain (FIG. 11a). The results of the OD yield study, FIG. 11b, also show that HL26715k has a healthy metabolism because of its glyoxylate cycle. OD yield relates to the amount of biomass generated per mole of glucose consumed. The OD yield of the parental strain is lower than the OD yield of the five mutant strains (FIG. 11b). For the parental strain, this indicates that much of the consumed carbon source is being metabolized to end products rather than biomass. This would be due to the high carbon throughput of the central metabolism in the parental strain. In the mutant strain, the OD yield found in these cultures started to rise with each additional mutation up to the strain HL2671k. The OD yield for HL2671k was the highest among all the mutant strains. This is likely due to the inactivation of its two major acetate pathways and disruption of its entire TCA cycle. Because of these perturbations, the downstream part of HL2671k's central metabolism is curtailed. This probably resulted in slow carbon throughput, therefore lower glucose uptake and more carbon flux driven toward biomass. When the iclR was inactivated in HL2671k creating the pentamutant strain, HL26715k, the OD yield decreased significantly by 66% (FIG. 11b). The OD yield of HL26715k is also now closer to the OD yield of the wildtype parental strain. This result shows that activating the glyoxylate bypass reconstituted the cycling effect of the TCA cycle. In HL26715k, restoration of the downstream metabolism again allowed faster carbon throughput, higher glucose consumption, and less biomass generation per mole of glucose consumed.

Acetate production decreased significantly upon inactivation of poxB and ackA-pta (FIG. 10b). This was shown to direct more carbon flux downstream to succinate production. The intermediate, pyruvate, was observed to be accumulating significantly in strains HL26k, HL267k, HL2671k, and HL26715k (FIG. 12a). Inactivation of the two acetate pathways and disruption of the TCA cycle by icd knockout apparently caused a bottleneck at the pyruvate junction (FIG. 1). This is why there is substantial pyruvate accumulation in mutant strains HL267k and HL2671k based on the amount of glucose they consumed. The pyruvate yield is 2.398 (mole pyruvate/mole glucose) for HL267k and 2.274 (mole pyruvate/mole glucose) for HL2671k (FIG. 12b). When HL26715k was created by activating the glyoxylate bypass, the pyruvate yield decreased significantly to 0.338 (mole pyruvate/mole glucose) indicating a substantial relief of pyruvate accumulation by the glyoxylate cycle. The maximum theoretical pyruvate yield is 2.0 (mole pyruvate/mole glucose) generated from glycolysis. The high pyruvate yield above 2.0 exhibited by strains HL267k and HL2671k can be due to the effect of nutrients originating from the complex medium such as phosphoenolypyruvate, which can be converted to pyruvate. In mutant strains with icd inactivated (HL2671k and HL26715k), there was also an accumulation of TCA cycle $C_6$ intermediates such as citrate and isocitrate (data not shown). Others have shown similar effects when icd was inactivated in *E. coli*. This accumulation is less, though, in HL26715k than in HL2671k due to the glyoxylate cycle. Nevertheless, the presence of pyruvate and TCA cycle $C_6$ intermediate accumulation in the pentamutant strain HL26715k shows that there are significant improvements that can be made to this strain to further increase the succinate yield. This aerobic succinate production system will serve as a novel platform for future metabolic engineering improvements on succinate production in *E. coli*.

The pentamutant strain, HL27615k, was characterized under controlled conditions in an aerobic batch reactor using strain. This would demonstrate the possibility of using this aerobic succinate production system in an industrial setting. In the bioreactor, 63 mM of glucose was added and 1% inoculum from an overnight culture grown from a single colony was used. Temperature and pH were maintained at 37° C. and 7.0, respectively. The DO was maintained above 80% saturation.

Figure 13:
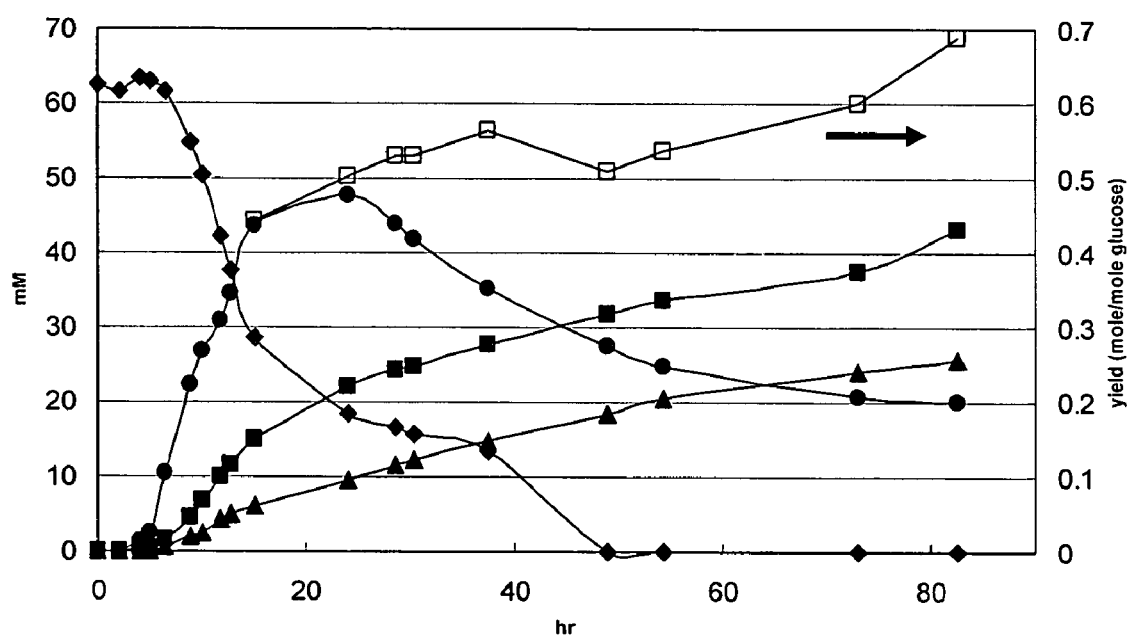
FIG. 13 depicts an aerobic batch reactor study on the pentamutant HL27615k. Solid diamond (♦) is glucose consumed. Solid square (■) is succinate produced. Solid triangle (▲) is acetate produced. Solid circle (●) is pyruvate produced. Open square (□) is the succinate yield (mole succinate produced per mole glucose consumed).

The results show that at 24 hours, succinate production is 22 mM with a molar yield of 0.5 (FIG. 13). This is better than the results from flask studies at 24 hours, which were 14 mM of succinate with a yield of 0.34. Using a bioreactor generates higher productivity due to a more controlled environment. Cells reached maximum OD of 9.12 after 12 hours with a specific growth rate of approximately 0.45 $hr^{-1}$. At 24 hours, pyruvate accumulation reached a maximum of 48 mM and glucose consumed was 44 mM. After 24 hours, the cells started consuming the excreted pyruvate along with the remaining glucose. All the glucose was consumed by about 49 hours at which point the pyruvate was still being consumed. By 83 hours, the pyruvate was not completely consumed, but succinate production reached 43 mM with a yield of 0.7. There was also accumulation of TCA cycle $C_6$ intermediates, which had not been consumed by the cells (data not shown). The results of the batch reactor study show that the pentamutant strain HL27615k has the potential to produce a large quantity of succinate under absolute aerobic conditions, and that there is potential to achieve the maximum succinate theoretical yield of 1.0.

The invention claimed is:

1. A mutant strain of *E. coli* bacteria wherein said mutant strain comprises inactivation of sdhAB, ackA-pta, and poxB.

2. The mutant strain of claim 1, wherein said mutant strain of *E. coli* bacteria further comprises inactivation of i) ptsG, or ii) iclR, or iii) icd, or iv) both ptsG and iclR, or v) both icd and iclR, or v) ptsG, iclR, and icd.

3. The mutant strain of claim 1, wherein said mutant strain of *E. coli* bacteria further comprises overexpression of pepc.

4. The mutant strain of claim 1, wherein said mutant strain of *E. coli* bacteria further comprises inactivation of iclR and overexpresses pepc.

5. The mutant strain of claim 1, wherein said mutant strain of *E. coli* bacteria further comprises inactivation of ptsG and iclR, and comprises overexpression of pepc.

6. The mutant strain of claim 1, wherein the bacteria produces succinate at a ratio of at least 0.6:1 moles succinate per mole glucose.

7. A mutant strain of *E. coli* bacteria, wherein said mutant strain comprises:
   i) inactivation of sdhAB, ackA-pta, poxB, and icd, and
   ii) overexpression of pepc.

8. The mutant strain of claim 7, wherein the bacteria produces succinate at a ratio of at least 0.6:1 moles succinate per mole glucose.

9. A mutant strain of *E. coli* bacteria, wherein said mutant strain comprises:
   i) inactivation of sdhAB, ackA-pta, poxB, ptsG, icd, and iclR, and
   ii) overexpression of pepc.

10. The mutant strain of claim 9, wherein the bacteria produces succinate at a ratio of at least 0.9:1 moles succinate per mole glucose.

* * * * *

UNITED STATES PATENT AND TRADEMARK OFFICE
CERTIFICATE OF CORRECTION

| | | |
|---|---|---|
| PATENT NO. | : 7,935,511 B2 | Page 1 of 1 |
| APPLICATION NO. | : 11/763424 | |
| DATED | : May 3, 2011 | |
| INVENTOR(S) | : Ka-Yiu San et al. | |

It is certified that error appears in the above-identified patent and that said Letters Patent is hereby corrected as shown below:

In the Specification:

Please replace the paragraph under the title FEDERALLY SPONSORED RESEARCH STATEMENT with the following:

This invention was made with government support under Grant No.: BES-0000303 awarded by National Science Foundation. The government has certain rights in the invention.

Signed and Sealed this
Second Day of July, 2013

Teresa Stanek Rea
*Acting Director of the United States Patent and Trademark Office*